United States Patent [19]

Kölbel et al.

[11] 4,177,203

[45] Dec. 4, 1979

[54] PROCESS FOR THE PRODUCTION OF HYDROCARBONS AND OXYGEN-CONTAINING COMPOUNDS AND CATALYSTS THEREFOR

[75] Inventors: Herbert Kölbel; Klaus D. Tillmetz, both of Berlin, Fed. Rep. of Germany

[73] Assignee: Schering Aktiengesellschaft, Berlin, Fed. Rep. of Germany

[21] Appl. No.: 840,059

[22] Filed: Oct. 6, 1977

Related U.S. Application Data

[63] Continuation of Ser. No. 657,470, Feb. 12, 1976, abandoned.

[51] Int. Cl.$^2$ .......................... C07C 1/04; C07C 27/06
[52] U.S. Cl. .......................... 260/449.6 R; 260/449 M; 260/449.6 M; 252/459; 252/454; 252/471
[58] Field of Search ....... 260/449 R, 449 M, 449.6 R, 260/449.6 M

[56] References Cited

U.S. PATENT DOCUMENTS

| | | | |
|---|---|---|---|
| 2,353,600 | 7/1944 | Sweetser | 260/449.6 |
| 2,369,106 | 2/1945 | Heckel et al. | 260/449.6 |
| 2,507,510 | 5/1950 | Frankenburg | 260/449 R X |
| 2,515,245 | 7/1950 | Mattox | 260/449 R X |
| 2,531,420 | 11/1950 | Frankenburg | 260/449 R X |
| 2,567,596 | 9/1951 | Clark | 260/449 R |
| 2,682,552 | 6/1954 | Black et al. | 260/449.6 |
| 3,254,023 | 5/1966 | Miale et al. | 260/449 R |

OTHER PUBLICATIONS

Riedl (Paliva 32 194–202, (1928)), Chem. Abs. 50, 8164h, 1956.
Hamai et al., Chem. Abst. 41, 4367d,e, 1947.

*Primary Examiner*—Howard T. Mars
*Attorney, Agent, or Firm*—Shapiro and Shapiro

[57] ABSTRACT

Processes for synthesizing unsaturated and saturated hydrocarbons and oxygen-containing compounds by catalytic hydrogenation of carbon monoxide at temperatures of 220 to 375 degrees C. and pressures from 1 to 60 bars. Specially activated catalysts for this purpose contain at least 50% manganese and less than 50% iron, by weight. The product distribution spectrum is shifted in the direction of $C_2$ to $C_4$ hydrocarbons, the chain length of the products extending only to about $C_6$ and methane being formed only in traces.

6 Claims, No Drawings

PROCESS FOR THE PRODUCTION OF HYDROCARBONS AND OXYGEN-CONTAINING COMPOUNDS AND CATALYSTS THEREFOR

This is a continuation application of Ser. No. 657,470, filed Feb. 12, 1976, now abandoned.

The present invention is concerned with synthesising unsaturated and saturated hydrocarbons and oxygen-containing compounds by catalytic hydrogenation of carbon monoxide at temperatures from 220° to 375° C. and pressures from 1 to 60 bars.

One object of the invention is to produce, preferably but not necessarily by gasification of coal, a mixture of carbon monoxide and hydrogen, and then to synthesise therefrom those raw materials for the petrochemical industry which today are obtained almost exclusively from petroleum or petroleum fractions. Belonging to these raw materials, but not limited thereto, are primarily unsaturated hydrocarbons and, among these, especially those with a chain length from $C_2$ to $C_4$, which form the main proportion of the raw materials which are indispensable for the petrochemical industry. The synthesis of such raw materials is thus of political economic importance, since it could relieve or even eliminate the dependence of the petrochemical industry on the supply of petroleum.

To attain this object it is proposed according to the invention to use novel catalysts comprising as the catalytically active component elementary manganese, preferably oxide or compounds thereof hydroxide in which manganese is present in amount of at least 50% by weight and iron is present in amount of less than 50% buy weight, and to subject these catalysts to conversion into the synthesis-active state (also herein referred to as forming or activating) by pretreating the catalyst with carbon monoxide and thereafter with hydrogen or with mixtures of these gases, at temperatures about 10° to about 60° C. higher than the "start-up" temperature of the synthesis. The catalyst in the synthesis-active state can then be used at the start-up temperature and at temperatures in excess thereof, such higher temperatures being chosen to optimise the desired synthesis.

The production of hydrocarbons and oxygen-containing compounds from carbon monoxide and hydrogen according to F. Fisher and H. Tropsch is known world-wide; it has been repeatedly and comprehensively described (e.g. Ullmanns Enzyklopädie der technischen Chemie, 3rd edition, volume 9, 685–748, Urban and Schwarzenberg, Munich and Berlin 1957; H. Kölbel in "Chemische Technologie" by K. Winnacker and L. Küchler, volume 3, pages 439–520, 2nd edition, Carl Hanser Verlag, Munich 1959). The main production target of all Fischer-Tropsch installations operated in Germany and abroad was and is the production of fuels with chain lengths from $C_6$ to about $C_{17}$. The catalysts which have been developed for this production target and which contain cobalt or iron as catalytically active elements are accordingly of little use for the purpose of the present invention, since with them, corresponding to the production target, mainly liquid and partially solid hydrocarbons are formed, having chain lengths from $C_6$ to about $C_{50}$, together with at most only 30 to 50% by weight of low molecular weight hydrocarbons of the chain length $C_2$ to $C_4$, which are desirable for the petrochemical industry.

All effort for shifting the product distribution spectrum in the direction of $C_2$ to $C_4$ hydrocarbons in such a way that this fraction, with sufficient gas conversion, is formed as the main proportion of all the synthesis products, has so far been unsuccessful. By way of example, for thermodynamic reasons, it is possible by means of high operating temperatures between 290° and 320° C. to lower the proportion of the products of higher molecular weight and to increase the proportion of the products of low molecular weight, but it is then necessary to accept the fact that, particularly with a high hydrogen-partial pressure, a large proportion of the synthesis gas (up to 70%) is converted into methane and, with gases with a high carbon monoxide content, the catalysts are damaged by the formation of carbon.

It is generally known that, with the processes as so far known, the proportion of the $C_2$ to $C_4$ hydrocarbons in the complete product decreases in the sequence $C_3$, $C_4$, $C_2$. This is disadvantageous, since the requirements of the petrochemical industry for unsaturated, low molecular weight hydrocarbons decrease in the sequence $C_2$, $C_3$, $C_4$. (The requirements for the German Federal Republic in 1973 were: 2.7 million tonnes of $C_2H_4$, 1.7 million tonnes of $C_3H_6$ and 0.6 million tonnes of $C_4H_8$).

Summarising, it has not so far been possible successfully, with regard to one object of the present invention, to modify the selectivity of the catalysts in the direction of the advantageous production of unsaturated, low molecular weight hydrocarbons and to conform to the needs of industry.

The present invention suitably obviates the above-mentioned disadvantages, solves the hitherto open problem of selectivity, and meets the object as initially referred to by means of catalysts comprising a predominant proportion of catalytically active manganese.

Manganese compounds have already been known for decades as promoters for catalysts for the hydrogenation of carbon monoxide (H. H. Storch, N. G. Golumbic, R. B. Anderson "The Fischer-Tropsch and Related Syntheses", pages 224, 242, 273, 277, John Wiley & Sons, New York, 1951).

Manganese compounds as promoters are most often employed only in small quantities, relatively to the catalytically active element (cobalt, nickel, iron); they produce an increase in the activity and, in certain circumstances, shift the product distribution spectrum in the direction of long-chain hydrocarbons. Manganese has not so far been used as a spontaneous catalytically acting element. According to the prevailing technical opinion, it would even be necessary for manganese to be "excluded" as a catalytically active element for Fischer-Tropsch catalysts (R. G. Anderson, J. E. Hofer, H. H. Storch, Chemi-Ing-Techn. 30, page 560, 1958).

By contrast, it is surprising that, in accordance with the present invention, manganese is itself catalytically active after pretreatment with carbon monoxide and hydrogen without any additives, and that in the presence of a combination comprising the elements Mn and Fe in amount of, for example, about 90% Mn and about 10% Fe, there are achieved conversions of more than 75% of the introduced $CO+H_2$ to hydrocarbons and oxygen-containing products having chain lengths substantially not in excess of $C_6$, methane only being formed in traces.

As already previously stated, one object of the invention is to produce preferably low molecular weight and unsaturated hydrocarbons, and oxygen-containing compounds, from gases which contain carbon monoxide and hydrogen, and to provide for this purpose catalysts which have a selectivity which is superior to that of the prior known catalysts.

In accordance with the process of the invention, mixtures of carbon monoxide and hydrogen are conducted at temperatures from 220° to 375° C. and pressures from 1 to 60 bars over catalysts which contain manganese or compounds thereof in combinations of more than 50% manganese and less than 50% iron as catalytically active elements. Commonly, it is the oxides or hydroxides of these elements which are used, but the percentages are based on the elements Mn and Fe and are expressed by weight. By treatment with carbon monoxide and a subsequent treatment with hydrogen (forming or activating), the catalysts are converted at space velocities (liters of gas per liter of catalyst and per hour) of more than 1000 at normal or elevated pressure, into the synthesis-active state, the conversion being carried out at temperatures which are 10° and 60° C. higher than the start-up temperature of the proposed synthesis.

By way of explanation, the activating temperature is between 10° to 60° C. higher than the temperature at which a synthesis reaction between carbon monoxide and hydrogen is initiated for any given feed composition, pressure and space velocity; the latter temperature is referred to in the specification and the appended claims as the start-up temperature. In general, after completion of the catalyst activation, the temperature is lowered to the start-up temperature, the carbon monoxide-hydrogen containing gas is contacted with the synthesis-active catalyst under conditions of pressure and space velocity chosen for the synthesis. Thereafter, the temperature may be maintained at substantially the start-up temperature, or it may be raised to an optimum operating temperature, and the pressure may be varied to yield optimum results with respect to the desired synthesis products.

For the forming operation, it is advantageous to use gases which do not contain any oxidising constituents, such as oxygen, carbon dioxide and water. It is also preferable, more especially with precipitation catalysts, for the catalysts to be heated up quickly and in an inert gas, as for example nitrogen, to the forming temperature and for the forming gases to be conducted over the catalyst only when the forming temperature is reached. The forming with carbon monoxide or with carbon monoxide-hydrogen mixtures, is ended when the $CO_2$ content of the residual gas asymptotically tends towards a threshold or limit value. Depending on the activity of the catalyst, this is the case after 3 to 24 hours. If the catalyst, after being treated with carbon monoxide, then has hydrogen admitted thereto, the treatment period amounts to 10 to 24 hours.

After the forming operation has ended, the temperature is lowered by 10° and 60° C. and the catalyst, at the required pressure of about 1 to 60 bars, is charged with carbon monoxide-hydrogen mixtures (synthesis gas) at space velocities of 160 to 1500. The temperatures is so regulated that the required conversion is achieved.

Pure, electrolytically produced, compact manganese metal with a quite small surface area already has catalytic activity without any additive (Example 1, at 320° C. and a space velocity of 160), with formation of ethylene and propylene. A catalyst produced by precipitation of manganese hydroxides and dried shows a similar behaviour (Example 2, at 270° C. and a space velocity of 460).

If a catalyst is precipitated from solutions of nitrates, which catalyst contains 10% of iron (calculated as Fe) and 90% of manganese (calculated as Mn), the activity increases to an unexpectedly high degree. By the addition of iron, a conversion of more than 75% (related to $CO+H_2$) is achieved, with a product yield of 176 g per cubic meter (at n.t.p.) of introduced $CO+H_2$. As a consequence, methane and products with a C-number higher than $C_4$ are only formed in traces. As regards ethylene, propylene and butylene, 86 g are formed per cubic meter (at n.t.p.) of $CO+H_2$; propanal and butanal are formed in a yield of 20 g for each cubic meter (at n.t.p.) of $CO+H_2$ (Example 3, 280° C.).

The composition of the products can be modified within wide limits by varying the Mn/Fe ratio. The chain length of the products increases with the iron content of the catalysts.

The ratio between carbon monoxide and hydrogen can be modified within wide limits. The highest possible yields are produced if the $CO/H_2$ ratio of the synthesis gas corresponds to the ratio in which carbon monoxide and hydrogen are consumed during the synthesis. It is in particular possible to process gases which have a high carbon monoxide content and which lead to products having a particularly high olefine content, since the carbon deposition, which is known to be harmful, is only slight with the novel catalysts.

Solutions of manganese-iron alloys which can be used industrially can also be employed as initial material for precipitation catalysts. The use of naturally occurring manganese ores as catalysts for the process of the invention is not excluded, nor is the use of melt catalysts, which are produced in analogous manner to the known ammonia catalysts. The production of the catalysts by thermal decomposition of manganese and iron salts or by sintering the metals or the oxides is likewise not excluded.

The process of the invention can be carried out with all varieties of industrial methods concerned with hydrogenation of carbon monoxide as known per se, as for example, in solid bed reactors, in liquid phase reactors, in fluidised bed reactors and in flue dust reactors. When processes involving staging or recycling of the synthesis gases are used, it is expedient for carbon dioxide and water to be removed before the gases are reintroduced into the reactor.

The synthesis products are removed from the residual gas or the recycled gas in a manner which is known per se.

Additions of about 0.1 to about 5% by weight of compounds of the alkali metals, based on Mn+Fe, as for example potassium carbonate, increase the activity of the catalysts and the proportion of the unsaturated products in the end product. With precipitation catalysts, the additives are introduced while stirring into the washed hydroxide gels.

Additions of 0.1 to 10% of copper compounds, based on Mn+Fe, which are added, with precipitation catalysts, to the solutions of these metals, facilitate the conversion in accordance with the invention into the synthesis-active state.

By additions of oxides which can only be reduced with difficulty, for example, oxides of magnesium, calcium, aluminium, titanium and silicon, the structure of the catalysts is stabilised and the shrinkage of the surface by recrystallisation because of temperature stressing is inhibited.

With precipitation catalysts, supports such as, for example, kieselguhr, silica gel and water-glass, can be incorporated in a manner as known per se, the said supports developing a large surface area of the synthesis-active elements and protecting these against collective crystallisation.

The technical advance which can be produced with the invention consists in a considerable increase in the selectivity of the hydrogenation of carbon monoxide to hydrocarbons and oxygen-containing compounds as regards the preferred formation of products with a chain length from $C_2$ to $C_6$. This is of significant political economic importance as raw materials for the petrochemical industry.

The process according to the invention is hereinafter more fully illustrated by the following examples, in most of which data are given for operation at a start-up temperature and also at an optimum temperature. In all examples, sulphur-free and phosphorus-free gases, namely, carbon monoxide, hydrogen and argon or helium or nitrogen were used.

EXAMPLE 1

Manganese metal produced electrolytically and with a purity of 99.2%, in the form of cathode fragments with an average grain diameter of 1.5mm, is used as catalyst. A copper tube with a length of 1 meter and a diameter of 8 mm is employed as reactor. After rapid heating of the catalyst bed in a stream of nitrogen, the catalyst is formed for 24 hours at 380° C. and 1 bar with a carbon monoxide-hydrogen mixture (49.2% CO, 46.3% $H_2$ and 4.5% He) with a space velocity of 1500 [liters of gas/liters of catalyst·hour]. After lowering the temperature to a start-up temperature of 320° C. and raising the pressure to 10.2 bars, the synthesis is commenced. The values of the final gas analysis and the yield of hydrocarbons, related to the introduced synthesis gas, are indicated.

Synthesis conditions:

| Temperature: | 320° C.; 375° C. (optimum temperature) |
|---|---|
| pressure: | 10.2 bars |
| CO conversion at 320° C.: | 25% |
| CO conversion at 375° C.: | 31% |
| space velocity | 160 |

| | Temp. = 320° C. | | Temp. = 375° C. | |
|---|---|---|---|---|
| Compound | Analysis of the final gas % by vol. | Yield g/m³ (at n.t.p.) | Analysis of the final gas % by vol. | Yield g/m³ (at n.t.p.) |
| methane | 1.8 | 11.5 | 2.7 | 14.1 |
| ethene | 0.6 | 6.7 | 2.6 | 23.8 |
| ethane | 0.3 | 2.9 | 0.4 | 3.9 |
| propene | 0.3 | 4.0 | 0.6 | 8.2 |
| propane | 0.1 | 1.7 | 0.2 | 2.9 |
| butene | 0.6 | 13.4 | 1.0 | 17.7 |
| butane | 0.2 | 4.5 | 0.2 | 3.6 |
| pentene | 0.3 | 8.0 | 0.3 | 6.4 |
| pentane | 0.1 | 2.8 | 0.3 | 6.7 |
| liquid products | traces | traces | traces | traces |
| olefines | | 32.1 | | 56.1 |
| paraffins | | 23.4 | | 31.2 |
| olefine content of the gaseous hydrocarbons: | | 57% | | 65% |

EXAMPLE 2

Used as catalyst is a manganese precipitation catalyst. The production is carried out by a known method. Initial substance for the production is $Mn(NO_3)_2 \cdot 4H_2O$ by analysis. From 1500 ml of a stock solution of 500 g/liter of $Mn(NO_3)_2 \cdot 4H_2O$, manganese hydroxide is precipitated at boiling temperature with an equivalent amount of 11% ammonia filter cake is dried by suction, homogenised and dried at 120° C. under vacuum. After subsequent comminution, a grain fraction from 0.8 to 2.0 mm is separated out by screening and is introduced for synthesis purposes into a copper reactor with a diameter of 10 mm and a volume of 4 cc. The catalyst is heated under nitrogen in the shortest possible time to 270° C. and thereafter, for forming purposes, carbon monoxide is introduced at the same temperature (pressure 1 bar) for 24 hours with a space velocity of 1200. A treatment with hydrogen under the same conditions, with a space velocity of 1500, follows for 24 hours. Thereafter, the conversion to synthesis gas (49.2% CO, 46.3% $H_2$, 4.5% He) is effected after lowering the temperature by 50° C. and raising the pressure to 10 bars.

Synthesis conditions:

| temperature: | 270° C. |
|---|---|
| pressure: | 10.4 bars |
| CO conversion | 24% |
| space velocity: | 460 |

| | % by vol. | CO + $H_2$ |
|---|---|---|
| methane | 1.8 | 10.7 |
| ethene | 2.0 | 21.5 |
| ethane | 0.5 | 5.8 |
| propene | 0.4 | 5.0 |
| propane | 0.4 | 4.2 |
| butene | 0.9 | 18.9 |
| butane | 0.5 | 11.1 |
| liquid products | traces | traces |
| olefines | | 45.4 |
| paraffins | | 31.8 |
| olefine content of the gaseous hydrocarbons | | 59% |

EXAMPLE 3

A manganese-iron precipitation catalyst with a ratio of Mn:Fe = 9.1 is used as catalyst. The production is carried out as described in Example 2, with the difference that 9 parts of the manganese stock solution as described has added thereto 1 part of an iron stock solution with a content of 660 g/liter of $Fe(NO_3)_3 \cdot 9H_2O$. The forming is effected by the same method as in Example 2. The temperature is thereafter lowered to 240° C., the pressure is increased to 10 bars and the catalyst has admitted thereto a synthesis gas with the composition 54.4% CO, 38.6% $H_2$ and 7% Ar.

| pressure: | 10.8 bars |
|---|---|
| CO + $H_2$ conversion at 280° C.: | 76% |
| CO + $H_2$ conversion at 300° C.: | 84% |
| space velocity: | 340 |

| | Temp. = 280° C. | | Temp. = 300° C. | |
|---|---|---|---|---|
| Compound | Analysis of the final gas % by vol. | Yield g/m³ (at n.t.p.) | Analysis of the final gas % by vol. | Yield g/m³ (at n.t.p.) |
| methane | in traces | in traces | 1.9 | 11.0 |

-continued

| | | | | |
|---|---|---|---|---|
| ethene | 3.1 | 31.8 | 2.7 | 25.2 |
| ethane | 2.4 | 26.3 | 2.0 | 21.6 |
| propene | 1.4 | 21.5 | 2.7 | 37.9 |
| propane | 0.1 | 1.7 | 0.1 | 1.7 |
| butene | 1.6 | 32.8 | 2.2 | 44.5 |
| butane | 0.3 | 6.4 | 0.1 | 2.2 |
| ethanol | 0.2 | 3.3 | 0.6 | 9.9 |
| propanol | 0.3 | 6.6 | 0.6 | 13.0 |
| propanal | 0.7 | 14.7 | 0.2 | 4.2 |
| butanal | 0.2 | 5.2 | 0.2 | 5.2 |
| liquid products | traces | | | traces |
| olefines | | 86.1 | | 107.6 |
| paraffins | | 34.4 | | 36.5 |
| alcohols | | 9.9 | | 22.9 |
| aldehydes | | 19.9 | | 9.4 |
| olefine content of the gaseous hydrocarbons: | | 57% | | 63% |

EXAMPLE 4

The same catalyst as in Example 3 is used. The catalyst is formed by the same procedure as described therein. After the forming operation, the temperature is lowered to 240° C. and a synthesis gas of the same composition as in Example 3 is admitted to the catalyst at a pressure of 1.5 bars.

Synthesis conditions:

| | |
|---|---|
| temperature: | 330° C. |
| pressure: | 1.5 bars |
| CO + $H_2$ conversion: | 33% |
| space velocity: | 310 |

| Compound | Analysis of the final gas % by volume | Yield g/m³ (at n.t.p.) |
|---|---|---|
| methane | in traces | in traces |
| ethene | 0.9 | 10.7 |
| ethane | 0.1 | 1.3 |
| propene | 0.9 | 16.1 |
| propane | 0.1 | 2.1 |
| butene | 0.1 | 2.7 |
| liquid products | traces | traces |
| olefines | | 29.5 |
| paraffins | | 3.4 |
| olefine content of the gaseous hydrocarbons: | | 90% |

EXAMPLE 5

Used as catalyst is a manganese-iron precipitation catalyst with the ratio Mn:Fe=2.3:1. The production is carried out as described in Examples 2 and 3, with the difference that 1 part of the iron stock solution as described is supplied to 1.9 parts of the manganese stock solution as described. The forming operation is carried out as in Examles 2 and 3. The temperature is then lowered to 220° C., the pressure is raised to 10 bars and conversion is carried out in respect of synthesis gas having the composition of 54.4% CO, 38.6% $H_2$ and 7.0% Ar.

Synthesis conditions:

| | |
|---|---|
| temperature: | 265° C. |
| pressure: | 10.6 bars |
| CO conversion: | 81% |
| space velocity: | 310 |

| Compound | Analysis of the final gas % by volume | Yield g/m³ (at n.t.p.) |
|---|---|---|

-continued

| | | |
|---|---|---|
| methane | 2.9 | 13.0 |
| ethene | 1.0 | 8.0 |
| ethane | 1.0 | 8.6 |
| propene | 2.4 | 28.2 |
| propane | 0.2 | 2.1 |
| butene | 1.2 | 18.8 |
| butane | 0.2 | 2.8 |
| liquid products | traces | 59.8 |
| olefines | | 55.0 |
| paraffins | | 26.5 |
| olefine content of the gaseous hydrocarbons: | | 67% |

EXAMPLE 6

Used as catalyst is a manganese-iron catalyst with the ratio of Mn:Fe=9:1 which was prepared as described in Example 3. The forming operation is carried out in a manner similar to that used in Example 2, but the space velocity of the carbon monoxide is 670 at 1.7 bars and 285° C. Then follows a treatment with hydrogen under identical conditions, with a space velocity of 1700. The temperature is thereafter lowered to 225° C., the pressure is raised to 10 bars, and a synthesis gas with the composition of 53.2% CO, 39.4% $H_2$ and 7.6% $N_2$ is applied to the catalyst.

Synthesis conditions:

| | |
|---|---|
| temperature | 295° C. |
| pressure: | 0.8 bars |
| CO conversion: | 43% |
| space velocity: | 650 |

| Compound | Analysis of the final gas % by volume | Yield g/m³(at n.t.p.) CO + $H_2$ |
|---|---|---|
| methane | 2.4 | 13.7 |
| ethene | 2.2 | 22.0 |
| ethane | 0.6 | 6.4 |
| propene | 1.6 | 24.0 |
| propane | 0.2 | 3.1 |
| butene | 0.4 | 8.0 |
| butane | 0.1 | 2.0 |
| ethanol | 0.2 | 2.5 |
| propanol | 0.4 | 8.5 |
| propanal | 0.2 | 4.1 |
| butanal | 0.2 | 5.0 |
| liquid products | traces | traces |
| olefine content of the gaseous hydrocarbons: | | 68% |

EXAMPLE 7

Used as catalyst is a manganese-iron catalyst with the ratio Mn:Fe=9:1, which was prepared as described in Example 3. The forming was carried out with a synthesis gas of the composition 36.6% CO, 54.8% $H_2$ and 8.6% $N_2$, at 1.8 bars and 320° C., with a space velocity of 1700, for 24 hours. The temperature was thereafter lowered to 290° C. and the pressure raised to 10.3 bars. The catalyst then had supplied thereto a synthesis gas of the composition 54.9% CO, 38.9% $H_2$ and 6.2% $N_2$.

Synthesis conditions:

| | |
|---|---|
| pressure: | 9.9 bars |
| temperature | 285° C. |
| CO conversion: | 53% |
| space velocity: | 850 |

| | Analysis of the final gas | Yield g/m³ (at n.t.p.) |
|---|---|---|

-continued

| Compound | % by volume | CO + H$_2$ |
|---|---|---|
| methane | 1.4 | 6.6 |
| ethene | 2.0 | 16.6 |
| ethane | 1.1 | 9.8 |
| propene | 2.0 | 24.9 |
| propane | 0.2 | 2.6 |
| butene | 0.5 | 8.0 |
| butane | 0.05 | 0.8 |
| ethanol | 0.9 | 12.3 |
| propanol | 0.6 | 10.3 |
| propanal | 0.2 | 3.4 |
| butanal | 0.03 | 0.6 |
| liquid products | traces | traces |
| olefine content of the gaseous hydrocarbons: | | 71% |

We claim:

1. A process for the synthesis of gaseous hydrocarbons and oxygenated derivatives thereof, in which the product distribution spectrum is shifted in the direction of chain lengths of C$_2$ to C$_4$, said process including the steps of pretreating a catalyst with an activating gas selected from the group consisting of (1) carbon monoxide and hydrogen in admixture and (2) carbon monoxide and hydrogen in succession, at an activating temperature of about 10° C. to about 60° C. in excess of the synthesis start-up temperature, the pretreatment with activating gas (1) being performed by contacting the activating gas with the catalyst until the carbon dioxide content of the residual gas asymptotically tends toward a limit value, the pretreatment with activating gas (2) being performed by contacting the carbon monoxide with the catalyst until the carbon dioxide content of the residual gas asymptotically tends toward a limit value and by contacting hydrogen with the catalyst for 10 to 24 hours, said catalyst comprising a composition selected from the group consisting of (a) an oxide or hydroxide of manganese and (b) oxides or hydroxides of manganese and iron, the composition containing manganese in amount of at least about 70% and iron in amount of less than about 30% of manganese plus iron, by weight, and thereafter lowering the temperature of the activated catalyst to the synthesis start-up temperature, and contacting the activated catalyst with a synthesis gas containing carbon monoxide and hydrogen at synthesis temperatures from about 220° C. to about 375° C. and at pressures from about 1 bar to about 60 bars.

2. A process in accordance with claim 1, wherein the catalyst comprises oxides or hydroxides of manganese and iron in which the ratio of manganese to iron is about 9:1, by weight.

3. A process in accordance with claim 1, wherein the activating gas is free of oxidizing constituents.

4. A process in accordance with claim 1, wherein the synthesis gas is contacted with the catalyst at space velocities within the range of 160–1500.

5. A process in accordance with claim 1, wherein the catalyst includes compounds of the alkali metals in an amount from about 0.1 to about 5% manganese plus iron, by weight.

6. A process in accordance with claim 1, wherein the catalyst includes structure stabilizers in the form of oxides selected from the group consisting of calcium, magnesium, aluminum, titanium, and silicon oxides.

* * * * *